United States Patent
Zhou et al.

[11] Patent Number: 5,849,026
[45] Date of Patent: Dec. 15, 1998

[54] PHYSIOTHERAPY METHOD

[76] Inventors: Lin Zhou; Xue-shan Zhang, both of 33 Woodshire Ter., Towaco, N.J. 07082

[21] Appl. No.: 921,405

[22] Filed: Aug. 29, 1997

Related U.S. Application Data

[60] Continuation of Ser. No. 374,475, Jan. 17, 1995, abandoned, which is a division of Ser. No. 508,302, Apr. 12, 1990, abandoned, which is a continuation-in-part of Ser. No. 103,808, Oct. 1, 1997, abandoned.

[30] Foreign Application Priority Data

May 20, 1987 [CH] Switzerland ............ 87.208.158
May 20, 1989 [CH] Switzerland ............ 87.103.603

[51] Int. Cl.$^6$ .................................. A61N 5/06
[52] U.S. Cl. .................... 607/90; 607/1; 607/88; 607/96; 607/100
[58] Field of Search ................ 607/1, 3, 2, 45, 607/44, 50, 80, 88, 90, 94, 96, 98–100; 128/898; 313/485, 486, 489, 491

[56] References Cited

U.S. PATENT DOCUMENTS

| | | | |
|---|---|---|---|
| 743,306 | 11/1903 | Merwin | 604/20 |
| 1,429,443 | 9/1922 | McFaddin | 128/395 |
| 3,658,068 | 4/1972 | McNall | 128/395 |
| 3,818,914 | 6/1974 | Bender | 128/396 |
| 3,821,576 | 6/1974 | Larson | 128/395 |
| 3,890,530 | 6/1975 | Hammer et al. | 313/489 |
| 3,967,153 | 6/1976 | Milke et al. | 313/492 |
| 3,995,191 | 11/1976 | Kaduk et al. | 313/489 |
| 4,287,554 | 9/1981 | Wolff | 362/218 |
| 4,420,709 | 12/1983 | Rattray | 313/487 |
| 4,505,545 | 3/1985 | Salia-Munoz | 350/321 |
| 4,540,915 | 9/1985 | Shinkai et al. | 313/486 |
| 4,558,700 | 12/1985 | Mutzhus | 128/395 |
| 4,601,917 | 7/1986 | Russo et al. | 106/287.19 |
| 4,607,191 | 8/1986 | Flaherty | 313/486 |
| 4,663,563 | 5/1987 | Taya et al. | 313/487 |
| 4,716,337 | 12/1987 | Huiskes et al. | 313/487 |
| 4,762,131 | 8/1988 | Okuda | 128/395 |

FOREIGN PATENT DOCUMENTS

| | | | |
|---|---|---|---|
| 1157584 | 5/1958 | France | 128/395 |
| 3027516 | 2/1982 | Germany | 128/395 |

OTHER PUBLICATIONS

"Notices of Judgment under the FDA," Nov. 1951, p. 467, Federal Register.

Luminescence of Alkaline–Earth Phosphates, Activated with Divalent Europium, Aug. 1967, Wanmaker et al..

"Certificate of Clinical Application and Basic Scientific Research W5–Freq. Spect. App.," Jun. 1983, Health Department of Yunnan, China.

*Primary Examiner*—William E. Kamm
*Assistant Examiner*—Kennedy J. Schaetzle
*Attorney, Agent, or Firm*—Workman, Nydegger & Seeley

[57] ABSTRACT

The present invention relates to a radiation generating apparatus for physical therapy and a process for its manufacture. The apparatus generates a characteristic radiation spectrum to treat or effectively treat or cure diseases of the blood circulating system, skin diseases, surgical wounds, arthritis, bronchitis, asthma, functional disorders of the stomach and/or intestines, gynecological and obstetric disorders such as dysmenorrhoea, hypertension, stress and for promoting the healing of wounds. The apparatus employs a radiation generator comprising a substrate, a transducing layer and a radiation generating layer. A dual purpose radiation treatment and lighting lamp is also described.

20 Claims, 12 Drawing Sheets

PHYSIOTHERAPY METHOD

This application is a continuation of Ser. No. 08/374,475, filed Jan. 17, 1995, now abandoned, which which is a divisional application of co-pending application Ser. No. 07/508,302 filed Apr. 12, 1990, now abandoned, which is a continuation-in-part application of co-pending application Ser. No. 07/103,808, filed Oct. 1, 1997, now abandoned, and claims priority to P.R.C. patent applications 87,103,603 and 87,208,158 both filed on May 20, 1987.

BACKGROUND OF THE INVENTION

The present invention relates to an apparatus for physical therapy and a process for its manufacture. The apparatus emits a characteristic energy spectrum to effectively treat and cure surface wounds and skin diseases, such as chilblains, frostbites, burns and scalds, chronic skin ulcer, and herpes; arthritis, periarthritis of the shoulder, inflammation of the cervical vertebra, contusion of soft tissue, bronchitis, pneumonia, asthma, functional disorders of the stomach and/or intestines such as diarrhea, gynecological and obstetric disorders such as dysmenorrhoea, inflammation of the vagina, hypertension, stress and for promoting the healing of wounds, and maintaining health.

Presently, popular physiotherapeutic equipment in use include mainly those which employ electricity, ultrasonic wave, infrared rays, ultraviolet rays, microwave, laser beams, or heat for the treatment of various disease conditions. Many of these employ electromagnetic radiation to act on the body. For example, various types of equipment employ ultrasonic wave frequencies of 20,000 Hz or above, or infrared rays having a spectrum of between about 780 to 30,000 millimicrons, or ultraviolet rays having a spectrum of between about 180 to 300 millimicrons, or microwave energy with wavelengths of about 1 to 100 millimeters. Electrical conductance, laser beams and heat have also been employed to treat various disease conditions. These physiotherapy methods have all been beneficial in conquering pain and suffering with varying degrees of success.

However, these known methods have many shortcomings, such as:

(1) Limited curative effects. Each physiotherapy methods can only be used to treat a limited number of disease conditions. Some common diseases, such as chilblains, frostbites, rhinitis, colds, etc., cannot be treated rapidly or effectively at all.

(2) Various deleterious side effects. Each of the known methods have unwanted side effects such as, potential damage from electrical shock, damage to the retina of the eyes, burns, skin cancer, etc.

(3) Costly and difficult to manufacture, and inconvenient to maintain and operate.

(4) Difficult to modify for use at home or in small medical clinics.

Other known existing physiotherapy devices made for home use can provide a level of health protection and illumination and are low cost, convenient to use and maintain. However, the variety and effectiveness of these home use devices are far from adequate to provide the desired level of medical benefits or sufficient amount of light for daily activities. Moreover, these physiotherapy devices utilizes narrowly defined regions of the energy spectra such as UV or infra red radiation and the effectiveness of the treatment is limited.

For example, in Applications DT2846221, WO9302233, DE3301802 and CN85100538, devices carrying a light bulb and using ultraviolet rays, and near-infrared rays for the treatment of disease conditions are described. However, due to the limitations of the radiation employed, these cannot be used to provide adequate general lighting and/or adequate general medical health care.

It is an objective of the present invention to provide an apparatus which generates a broad spectrum of electromagnetic radiation over a wide range and a method for its production. It is believed that the apparatus emits electromagnetic wave radiation which is identical to or similar to the suspected natural frequency spectrum of a healthy human body. Thus, when a patient is exposed to the radiation generated by the apparatus, it can be used to effectively cure many common diseases for which there has been poor clinical records.

It is another objective of the present invention to manufacture a multi-functional apparatus capable of curing effectively many disease conditions in the areas of internal medicine, surgery, pediatrics, gynaecology, obstetrics, and dermatology.

It is another objective to provide a radiation generating apparatus which is small and convenient to use.

It is a further objective of the invention to provide a simple apparatus for the manufacture of a radiation generating apparatus which requires little investment of money, yet is capable of producing rapid and effective results.

Another objective of the present invention is to provide a dual-purpose lamp, to simultaneously provide general lighting and general health protection, in addition to providing relief for many diseases. The apparatus can be used to provide partial or complete relief for diseases of the blood circulatory system, surgical wounds, skin diseases, arthritis, and autonomic neurotic diseases.

A final objective of the present invention to provide a radiation generating apparatus with a simple and reasonable design which also adequately takes into accounts the level of lighting needed for daily activities.

SUMMARY OF THE INVENTION

A physiotherapy apparatus comprising

A. A transduction circuit control means connected to a power supply;

B. A substrate made of a heat resistant and insulating material and provided therein electrical connecting means, one end of which is connected to the transduction control circuit;

C. A transducing layer coated on one surface of the substrate and electrically contacting the other end of the electrical connecting means in the substrate; the transducing layer made from a mixture comprising about 80–120 parts by weight of tin tetrachloride, about 0.5 to 2 parts by weight of antimony trichloride and about 0.3 to 2.5 parts by weight of iron trichloride; and D. A radiation generating layer deposited over the transducing layer comprising a homogeneous mixture of magnesium oxide, iron oxide, manganese oxide, molybdenum oxide, zinc oxide, lithium oxide, copper oxide, titanium oxide, strontium oxide, chromium oxide, cobalt oxide, vanadium oxide, chromium metal and mixed rare earth elements and/or compounds in a proportion by weight respectively of about 0.5–8%: about 7–30%: about 0–6%: about 0.6–5%; about 1–17%: about 0–4%: about 1–7%: about 0–7%: about 0–5.5% about 25–85%: about 0–5%: about 0–10%: about 0.5–4%: about 0–40%, the selected proportions being determined according to the types of disease conditions sought to be treated;

The size of the radiation generating layer being larger or equal to the area to be treated, the effective transducing area of the transducing layer being larger or equal to the size of the radiation generating layer and the substrate being larger or equal to the effective transducing area.

A method of manufacturing a physiotherapy apparatus comprising:

A. providing a power supply means;

B. providing a transducing circuit control means connected to the power supply;

C. forming a substrate from a heat resistant, insulating material and providing therein electrical connecting means;

D. connecting one end of the electrical connecting means to the transducing circuit control means;

E. coating a transducing layer on the substrate such that the transducing layer is in contact with other end of the electrical connecting means in the substrate, the transducing layer comprising a mixture of about 80–120 parts by weight of tin tetrachloride, about 0.5 to 2 parts by weight of antimony trichloride and about 0.3 to 2.5 parts by weight of iron trichloride;

F. heating the substrate and the transducing layer at a temperature of about 600° to 900° C. for about 1 to 6 hrs; and then cooling to room temperature;

G. evenly coating the transducing layer with a radiation generating layer comprising a homogeneous mixture of magnesium oxide, iron oxide, manganese oxide, molybdenum oxide, zinc oxide, lithium oxide, copper oxide, titanium oxide, strontium oxide, chromium oxide, cobalt oxide, vanadium oxide, chromium metal and mixed rare-earth elements and/or compounds in a proportion by weight of about 0.5–8%: about 7–30%: about 0–6%: about 0.6–5%: about 1–17%: about 0–4%: about 1–7%: about 0–7%: about 0–5.5%: about 25–85%: about 0–5%: about 0–10%: about 0.5–4%: about 0–40%, the proportions being determined according to the types of disease sought to be treated; the size of the radiation generating layer being larger than or equal to the diseased area to be treated, the effective transducing area being larger than or equal to the area of the radiation generating layer, and the substrate being larger than or equal to the effective transducing area.

BRIEF DESCRIPTIONS OF THE DRAWINGS

FIGS. 7a and 7b and 7c are partial views of a ternary holder for two radiation generators and a light bulb.

Figure 1:
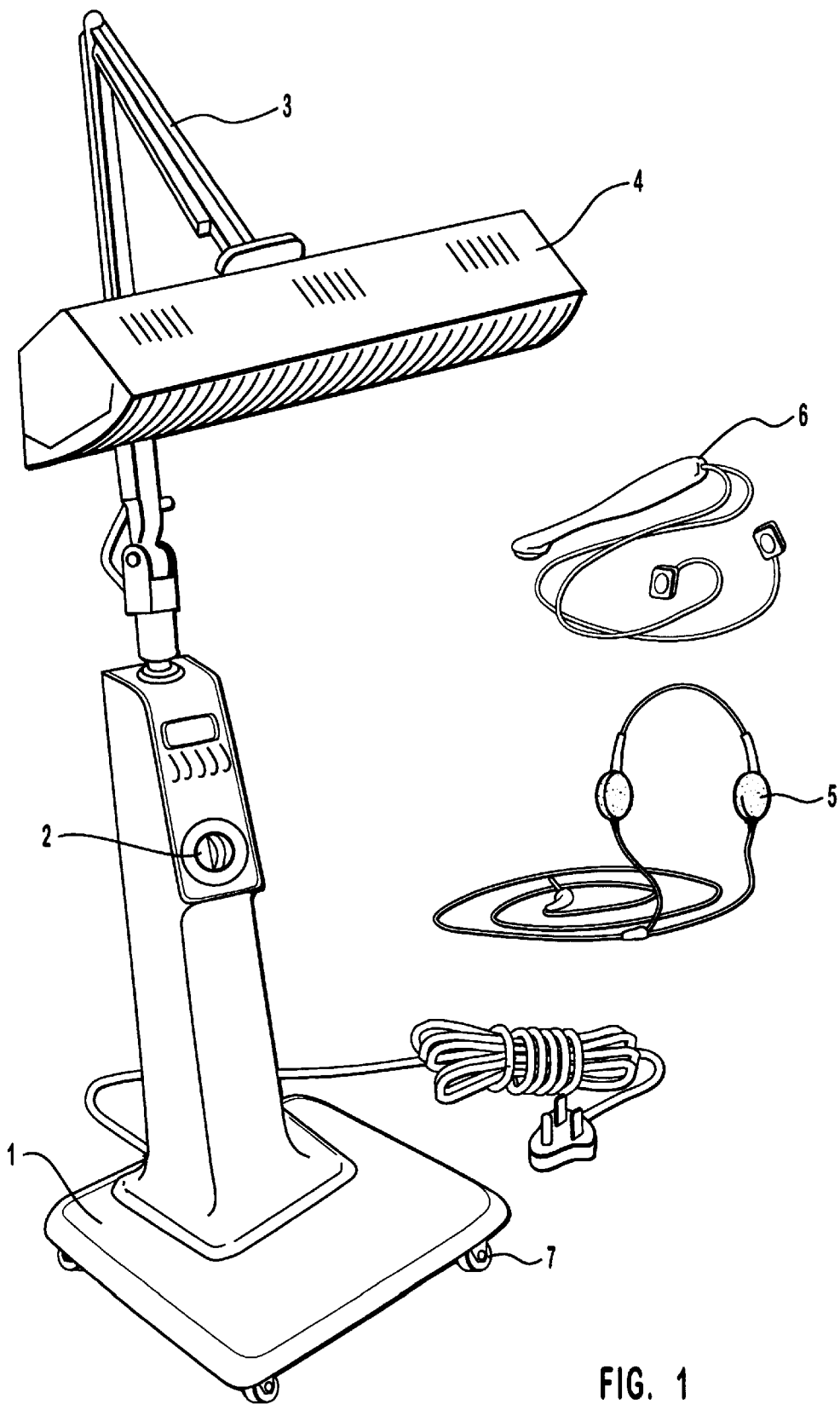
FIG. 1 is a perspective view of the one embodiment of the physiotherapy apparatus and auxiliary equipment.
Figure 2A:
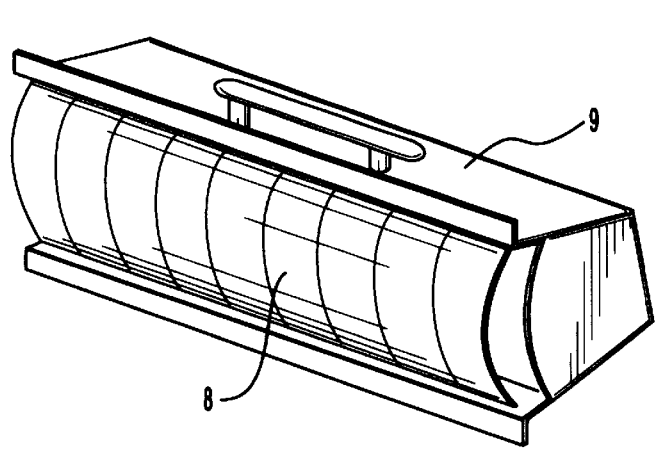
FIGS. 2a, 2b, 2c and 2d are partial views of the radiation generator, transducing layer radiation generating layer and substrate.
Figure 2C:
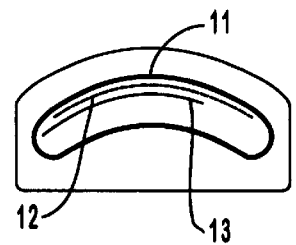
Figure 2B:
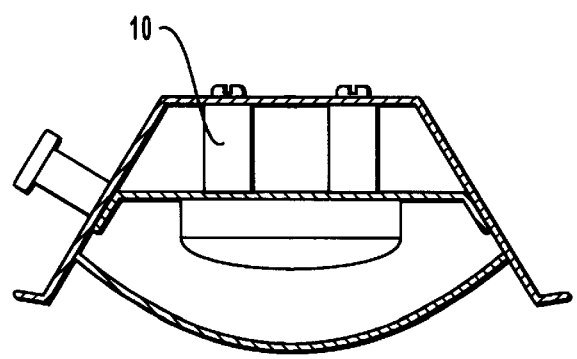
Figure 2D:
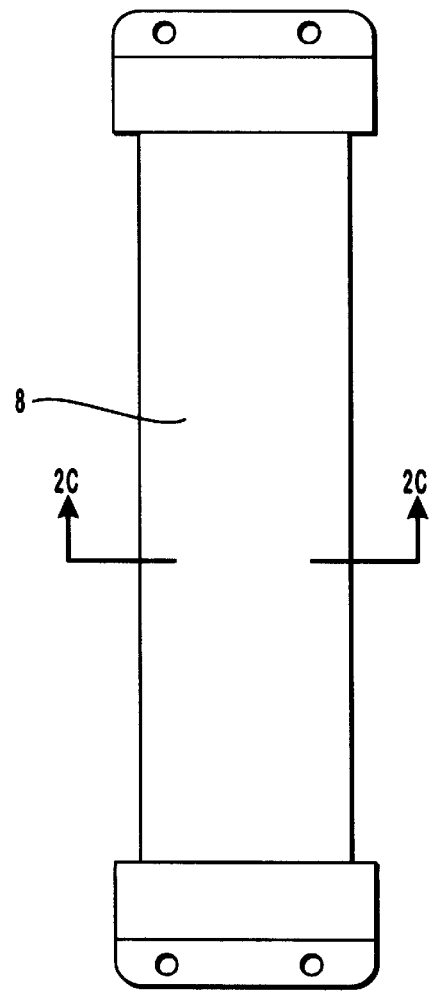
Figure 3:
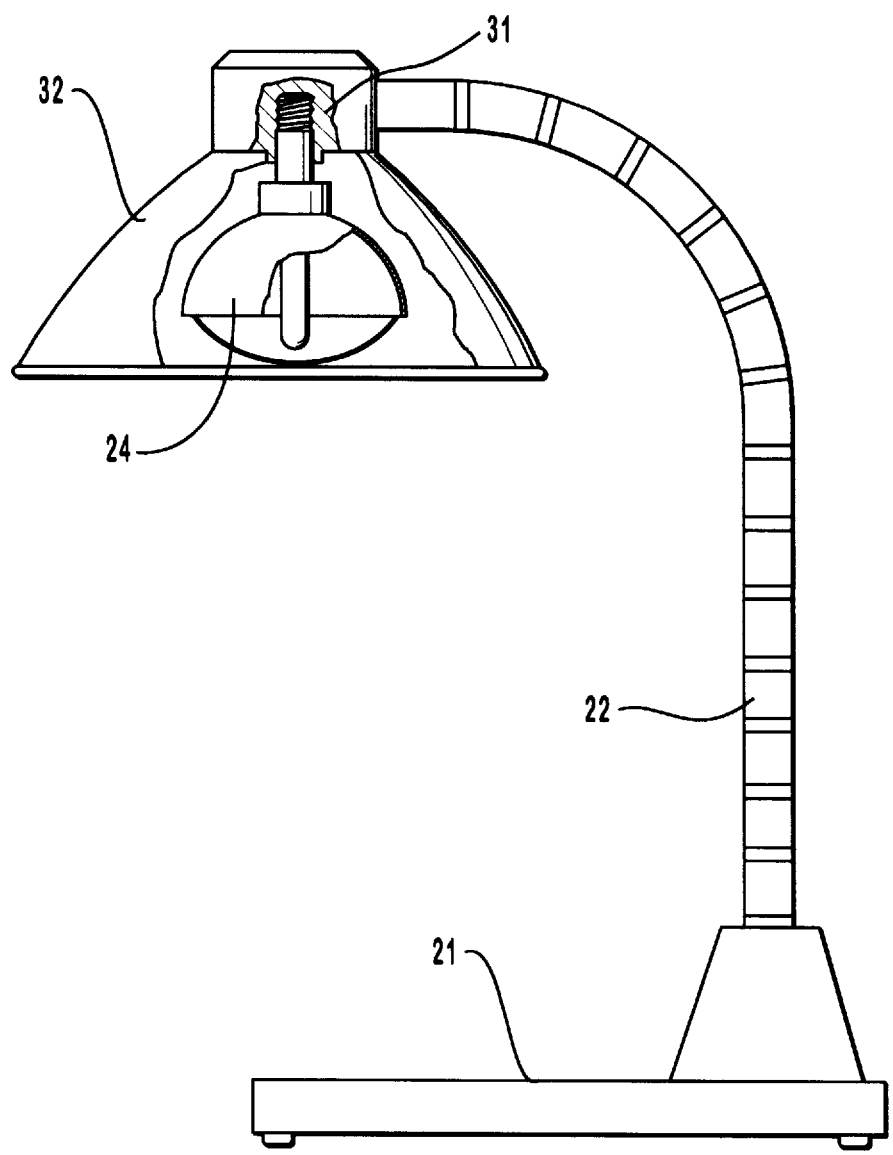
FIG. 3 is a perspective view of a dual purpose of treatment and lighting lamp for providing general lighting and single group treatment radiation generator.
Figure 4A:
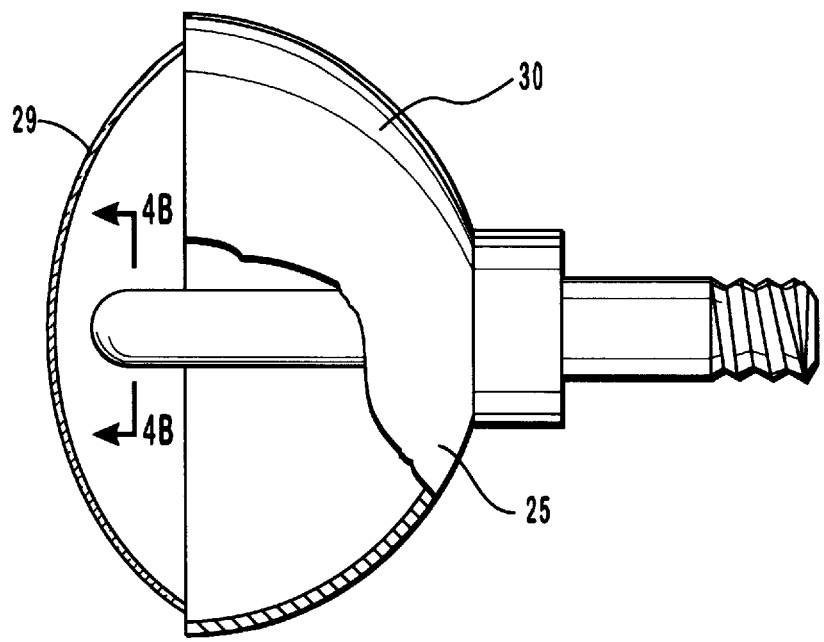
FIGS. 4a and 4b are partial views of radiation generator for a dual purpose treatment and lighting lamp.
Figure 4B:
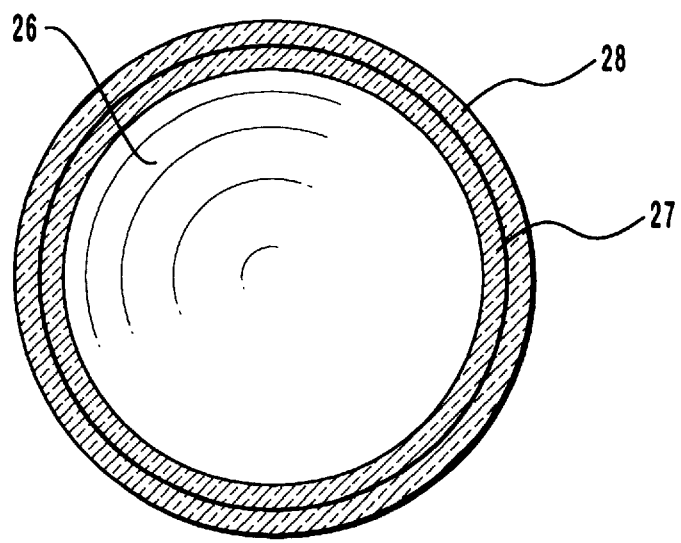

In the above drawings, the enumerated parts are:

(1) base;
(2) instrument control panel;
(3) supporting arm;
(4) radiation generator;
(5) earphones for musical source;
(6) accupoint stimulating electrodes;
(7) universal wheels;
(8) radiation generator;
(9) reflective protective cover;
(10) fixed strut;
(11) radiation generating layer;
(12) transducing layer;
(13) substrate;
(14) electrical connecting wires
(15) ceramic encasements for holding the transducing layer;
(16) electrodes;
(21) pedestal;
(22) flexible rod;
(23) support;
(24) single-group treatment generator holder;
(25) generator;
(26) substrate;
(27) transducing layer;
(28) radiation generating layer;
(29) protective network;
(30) reflective cover;
(31) receptacle;
(32) lamp cover;
(33) binary lamp cover;
(34) rotable support and hinge;
(35) tubular Light emitting bulb or a tubular generator.

DETAILED DESCRIPTION OF THE INVENTION

The present invention relates to a physiotherapy apparatus to generate a characteristic broad spectrum of electromagnetic radiation to treat various disease conditions of the skin, internal organs and autonomic neurotic conditions.

The radiation generating apparatus according to the present invention comprises:

A. A transduction circuit control means connected to a power supply;

B. A substrate made of a heat resistant and insulating material and provided therein electrical connecting means, one end of which is connected to the transduction control circuit;

C. A transducing layer coated on one surface of the substrate and electrically contacting the other end of the electrical connecting means in the substrate; the transducing layer made from a mixture comprising about 80–120 parts by weight of tin tetrachloride, about 0.5 to 2 parts by weight of antimony trichloride and about 0.3 to 2.5 parts by weight of iron trichloride; and D. A radiation generating layer deposited over the transducing layer comprising a homogeneous mixture of magnesium oxide, iron oxide, manganese oxide, molybdenum oxide, zinc oxide, lithium oxide, copper oxide, titanium oxide, strontium oxide, chromium oxide, cobalt oxide, vanaduim oxide, chromium metal and mixed rare earth elements and/or compounds in a proportion by weight respectively of about 0.5–8%: about 7–30%: about 0–6%: about 0.6–5%; about 1–17%: about 0–4%: about 1–7%: about 0–7%: about 0–5.5%: about 25–85%: about 0–5%: about 0–10%: about 0.5–4%: about 0–40%, the selected proportions being determined according to the types of disease conditions sought to be treated;

The size of the radiation generating layer being larger or equal to the area to be treated, the effective transducing area of the transducing layer being larger or equal to the size of the radiation generating layer and the substrate being larger or equal to the effective transducing area.

The method of manufacturing a physiotherapy apparatus comprises:

A. providing a power supply means;

B. providing a transducing circuit control means connected to the power supply;

C. forming a substrate from a heat resistant, insulating material and providing therein electrical connecting means;

D. connecting one end of the electrical connecting means to the transducing circuit control means;

E. coating a transducing layer on the substrate such that the transducing layer is in contact with other end of the electrical connecting means in the substrate, the transducing layer comprising a mixture of about 80–120 parts by weight tin tetrachloride, about 0.5 to 2 parts by weight antimony trichloride and about 0.3 to 2.5 parts by weight iron trichloride;

F. heating the substrate and the transducing layer at a temperature of about 600° to 900° C. for about 1 to 6 hrs; and then cooling to room temperature;

G. evenly coating the transducing layer with a radiation generating layer comprising a homogeneous mixture of magnesium oxide, iron oxide, manganese oxide, molybdenum oxide, zinc oxide, lithium oxide, copper oxide, titanium oxide, strontium oxide, chromium oxide, cobalt oxide, vanadium oxide, chromium metal and mixed rare-earth elements and/or compounds in a proportion by weight of about 0.5–8%: about 7–30%: about 0–6%: about 0.6–5%: about 1–17%: about 0–4%: about 1–7%: about 0–5.5%: about 25–85%: about 0–5%: about 0–10%: about 0.5–4%: about 0–40%, the proportions being determined according to the types of disease sought to be treated;

the size of the radiation generating layer being larger than or equal to the diseased area to be treated, the effective transducing area being larger than or equal to the area of the radiation generating layer, and the substrate being larger than or equal to the effective transducing area.

The substrate for the radiation generator can be made from any known heat resistant insulating material. It is formed into the desired shape and size and embedded therein with electrical connecting means, one end of which is connected to a transduction control circuit drawing power from a power source, the other end being for connection to the transducing layer deposited on the substrate. The electrical connections are provided at opposite ends or opposite sides of the transducing layer a layer of silver/mercury amalgam is sprayed deposited on a pair of electrodes, oxidized at 180° C. for one hour. Each of the electrodes is then soldered onto copper connecting wires and placed into the cavity of the ceramic encasements and cemented to the ceramic encasements. The wires are connected to each of the silver plated opposite ends or opposite side of the transducing layer.

The transducing layer is made by homogenously mixing pulverized tin tetrachloride, antimony trichloride and iron trichloride in a proportion in parts by weight of about 80–120:0.5–2:0.3–2.5, preferably about 105:0.8:1. An aqueous solution is prepared from the mixture by adding an effective amount of water.

The aqueous solution is then sprayed on the cleaned substrate. The coated substrate is heated at a temperature of about 600° C. for 1–6 hours, preferably 3 hours.

The transducing layer may be replaced by a heating element which comprises a high resistance heating wire coiled around a ceramic cylindrical stick placed into a ceramic tube in the shape like a laboratory test tube which is then coated with the radiation generating layer. The parts are then cemented together and connected to electrical leads to the transduction control unit. This embodiment is less effective but also less costly to manufacture. This embodiment provides a way of miniaturizing the radiation generator. It is suitable for minor aches and injuries.

The radiation generating layer is prepared by pulverizing and mixing magnesium oxide, iron oxide, manganese oxide, molybdenum oxide, zinc oxide, lithium oxide, copper oxide, titanium oxide, strontium oxide, chromium oxide, cobalt oxide, vanadium oxide, chromium metal, mixed rare-earth elements and/or compounds thereof in a proportion in percent by weight of about 0.5–8%:7–30%:0–6%:0.6–5%:1–17%:0–4%:1–7%:0–7%:0–5.5%:25–85%:0–5%:0–10%:0.5–4%:0–40%, the preferred proportions being determined by the types of diseases sought to be treated.

The preferred proportion in percent by weight of the above materials in named order for providing the best overall curative effects is: 1:20:2:3:4:0.5:1:1.5:0.5:45:0.5:10:1:10, The preferred proportions in percent by weight of the materials in above named order for providing notable effective relief for diseases of the blood circulatory system is: 2:30:0:0.6:6:1.5:1.2:2:1.2:37:0.3:5:1.2:12.

The preferred proportions in percent by weight of the materials in the above named order for providing effective relief for the healing of surgical wounds, diseases of the skin, injury to soft tissue, arthritis, etc, is: 0.5:25:3:2:7:2:1.5:1:1:55:0:0:1.5:0.5.

The preferred proportion in percent by weight of the materials in the above named order for providing effective relief for autonomic neurotic diseases is: 1.5:15:1:1.5:5:0:1.6:0:0:62:0.7:3:0.7:8.

The mixture of rare earth elements and/or compounds are elements and compounds in the lanthanide series, such as oxides and chlorides and maybe omitted. If the rare earth elements and/or compounds are omitted, the remaining materials should be present in the stated proportions in ratio by weight.

The selected materials can be mixed is one single large group or divided into smaller groups of materials. The group or groups of materials are homogeneously mixed and pulverized in a ball mill into particles of about 40–80 mesh, preferably 45–50 mesh. Each mixture is then calcined for about 2–6 hrs, preferably 3 hrs, at a temperature of about 1100°–1300° C. The calcined material or groups of materials is again pulverized into particles of about 40–60 mesh, preferably 45–50 mesh. A binder, such as silicasol, is added to the mixture and homogenously mixed therewith by stirring. The group(s) of mixture of pulverized materials and the binder is (are) evenly coated on the clean transducing layer. When several groups are used the layers are stratified into sublayers. When one single group is used only one layer will be coated on the clean transducing layer. The pulverized mixture may also be vacuum plated or plasma sprayed on the transducing layer.

The transduction control is an ordinary potentiometer which can be used to control the intensity and temperature of the radiation generated. For treatment of the various diseases, a suitable temperature range is 36° C. to 60° C., preferably 40° C.

The physiotherapy apparatus of the present invention is highly effective. It is believed that the result obtained is a result of the broad spectrum of electromagnetic radiation emitted by the radiation generator. The broad spectrum probably simulates that of the radiation emitted by the human body. It is known that the healthy human body radiates a characteristic spectrum. This spectrum of radiation is determined by its chemical make up and the temperature. At 32° C., it is known that the skin emits infra red radiation at a rate coefficient of about 0.98. Using black body radiation theory, the maximum wavelength ($\lambda$max) is 9.3482 um.

The radiation frequency emitted by the body comprises principally the following regions infra red, magnetic and radiowave. The frequency spectrum is continuous and broad covering a wide band of electro magnetic wavelengths. The various body tissues also have characteristic absorption spectra. FIGS. 9, 10, 11 and 12 are the infra red absorption spectra of the skin, muscle, mesentary tissue and blood respectively.

According to known theory, the radiation frequency spectrum of a body is generally similar to the absorption spectrum. Therefore, it was concluded that the human body frequency spectrum should be a summation of the absorption spectra of the various tissues of the body.

The present invention is directed to radiation generating apparatus which emits radiation with a spectrum which simulates the natural human body frequency. It is perhaps because of this phenomenon that the apparatus of the present invention is highly effective.

The apparatus may also include a music source, such as a stereophonic music playback system and/or an accupoint point stimulating device together with the control circuits for each. The music playback system may also be combined with the accupoint stimulating device, whereby music is used to stimulate the accupoints. In the latter case, only one control circuit is required.

The physiotherapy apparatus may also include mechanical transporting means such as a base with rollers. The entire apparatus together with the music playback system and accupoint stimulating device may be designed as a console for mounting on a wall or provided with a base with rollers for easy transportation.

The physiotherapy generating apparatus can also be in the form of a dual purpose lamp comprising a pedestal, a flexible rod connected to the pedestal alternatively supporting a light bulb or a radiation generator with a cover, a transduction control panel connected to a power supply, mounted to the flexible rod or pedestal, mechanical support means for the bulb or generator rotatability connected to the top of the flexible rod, with one to three radiation generators in tubular form attached to the mechanical support means, the generator being made of a heat resistant, insulating substrate having electrical connecting means connected to the transduction control panel, coated with a transducing layer, and then a radiation generating layer.

The radiation generating layer deposited over the transducing layer is made from a mixture of magnesium oxide, iron oxide, manganese oxide, molybdenum oxide, zinc oxide, lithium oxide, copper oxide, titanium oxide, strontium oxide, chromium oxide, cobalt oxide, vanadium oxide, chromium metal, and mixed rare-earth elements and/or compounds, such as lanthanides. The particular mixture selected being determined by the diseases sought to be treated.

The mechanical support means for the generator may comprise a single receptacle for mounting alternatively an ordinary light bulb or a radiation generator, the mechanical support means being mounted in the neck and positioned at the center of a concave reflective cover.

The lamp may also be provided with a support for two holders for mounting a radiation generator and a light bulb, each pointing in a different direction or back-to-back in opposite directions. The base for the radiation generator or the light bulb is connected to a receptacle in the neck of the reflective cover at the center of the concave reflective cover.

A rotatable support for holding three or four radiation generators or light bulb in which the radiation generators and a light bulb are attached to a rotatable support hinge may also be provided.

The rotatable support hinge is held on the top of the flexible rod by rotatable clips and stays.

When power is supplied to the radiation generating layer via the transducing layer, it produces an electromagnetic wave spectrum which appears to simulate the natural frequency spectrum of the various parts of the entire healthy human body. The radiation generating layer may be made of three different mixtures of magnesium oxide, iron oxide, manganese oxide, molybdenum oxide, zinc oxide, lithium oxide, copper oxide, titanium oxide, strontium oxide, chromium oxide, cobalt oxide vanadium oxide, chromium metal, rare-earth elements and/or compounds, such as lanthanides in proportions in percent by weight in the order named above according to the following groups:

Group I, for treating diseases of the blood circulatory system—2:30:0:0.6:6:1.5:1.2:2:1.2:37:0.3:5:1.2:12;

Group II, for healing of surgical wounds, diseases of the skin, injury to soft tissue, arthritis, inflammation of the cervical vertebra—0.5:25:3:2:7:2:1.5:1:1:55:0:0:1.5:0.5;

Group III, for relief of autonomic neurotic diseases—1.5:15:1:1.5:5:0:1.6:0:0:62:0.7:3:0.7:8.

The radiation generator comprises mainly a radiation generating layer, a transducing layer and a substrate. The radiation generating layer comprises a mixture selected from the fourteen different materials mentioned hereinabove. The selected materials are pulverized in a ball mill into particles, preferably about 50 mesh, and then mixed with a binder, such as silicasol. The mixture is coated over the surface of the transducing layer. The transducing layer is compounded from an aqueous solution of a mixture of $SnCl_4$: $SbCl_3$: $FeCl_3$ in a proportion in parts by weight of about 80–120:0.5–2:0.3–2.5 and heated. The solution is coated onto a heat resistant, insulating substrate, hydrolyzed and oxidized under high temperatures to form an electrical conducting layer of polycrystalline metallic oxides in the nature of a semiconductor. The transduction may also be controlled by adding impurities into the mixture. The heat resistant, insulating substrate can be formed from ordinary heat-resistant, insulating materials, such as glass.

This invention may also be used in conjunction with other known pharmaceutical preparations suitable for the diseases being treated.

To fully develop the effectiveness of the apparatus of the present invention, music may also be provided simultaneously. The combination is helpful to restore the systemic functions of the brain, eliminate feelings of stress and weariness, improving the state of mind and body, in addition to the treatment of mental and physical disease conditions. Further music provides a pleasant and comfortable environment during treatment.

Compared with prior art devices and processes, the apparatus and process of the present invention has many advantages: the effective cure rate is high and the operation of the apparatus is easy. More importantly, it can be used effectively to treat many common disease conditions, such as chilblains and frostbites for which no effective cures have been developed up to the present. The present invention has provided a simple, rapid and effective treatment method. For example, for chilblains and frostbites, painful itching is stopped, the injured or inflamed surfaces are dried after the first day of treatment. Complete cure can be achieved with only about 2 to 7 treatments, the effective cure rate being about 98%.

Furthermore, by proper adjustment of the frequency of the radiation generated to different parts of the body for treatment of different groups of diseases as stated herein, adjusting to the size and surface color of the area, and adjusting the dosage of the radiation applied, the apparatus of the present invention has been preliminarily found to offer improved relief for many diseases including obstruction of blood circulation in the capillaries and inflammatory or infectious conditions. See Table I for a partial clinical record of diseases treated.

TABLE I

A Partial Clinical Record of Disease Conditions Treated By The Radiation Generating Apparatus

| DISEASE CONDITION | FULLY RECOVERED | RE-LIEVED | NO PERCEPTIBLE EFFECT |
|---|---|---|---|
| Chilblains | more than twenty thousand, 98% | 2% | |
| Frostbite (mainly about 1 or 2 degree frostbite) | more than 400, 98% | 2% | |
| Ulcer caused by vasculitis on the lower limbs | 1 | 2 | |
| Ulcer caused by varix on the lower limbs | 2 | 3 | |
| Laceration in the vulva and | 8 | 7 | |
| Healing of the wound caused by the caesarean operation | 6 | | |
| Burns or scalds | 176 | 41 | 3 |
| Phlegmon | 5 | 18 | |
| Anal fistula | 3 | 12 | |
| Bed sores | 12 | 41 | 2 |
| Herpes zonster | 54 | 15 | |
| Pneumonia of children | 11 | 2 | |
| Bronchitis | 5 | 12 | |
| Bronchial asthma | 6 | 13 | |
| Primary hypertension | 4 | 7 | |
| Dysmenorrhoea | 19 | 57 | |
| Pelvitis | 3 | 21 | |
| Arthritis | 4 | 41 | 5 |
| Neurodermatitis | 12 | 35 | 2 |
| Rhinitis | 3 | 29 | |
| Relief of common cold | 4 | 22 | 9 |
| Headache | 27 | 21 | 4 |
| Stomach ache | 20 | 14 | |

TABLE I-continued

A Partial Clinical Record of Disease Conditions Treated By The Radiation Generating Apparatus

| DISEASE CONDITION | FULLY RECOVERED | RE-LIEVED | NO PERCEPTIBLE EFFECT |
|---|---|---|---|
| Hepatitis type A | 1 | | |
| Hepatalgia or biliary pain | | 5 | |
| Chalazion | 8 | | |
| Chronic diarrhea | 10 | 27 | |
| Beriberi | 8 | 24 | |
| Semiplegia | | 1 | |
| Acute or chronic contusion of soft tissue | 247 | 89 | |
| Periarthritis of the shoulder | 11 | 43 | |

The present invention offers a simple, effective, and low cost apparatus and method for treating and preventing diseases with no known side effects. Thus the use of the present invention can save an enormous amount of medical resources.

The present invention also provides a dual purpose lamp both for illumination as well as prevention and treatment of diseases. Further, because the radiation generators can be made of three different groups of selected materials in selected proportions, it can be used to concurrently cure different disease conditions in the areas of internal medicine, surgery, gynecology, obstetrics, dermatology, and pediatrics.

According to the selected different supports and different generators, the apparatus is useful in treating separately or simultaneously the diseases of the circulatory system with the Group I mixture mentioned above, surgical wounds, skin diseases and arthritis with the Group II mixture mentioned above, and autonomic neurotic diseases with Group III mixtures mentioned above. The various lamps are simple in design, easy to manufacture and convenient to use. Moreover, the multi-purpose lamp is suitable for home use.

An example of the apparatus of the present invention is as follows:

The apparatus comprise a flat base (1) with universal wheels (7) and fixed centrally with a rod to mechanically support an instrument control panel (2) connected to a power source, and a supporting arm (3) for radiation generator (4) and optionally earphones (5) connected to a source of music and accupoints stimulating electrodes (6), all of which are connected respectively to the instrument control panel.

The base comprises a flat base-plate with a rod fixed centrally therein. Universal wheels (7) are attached Lo the bottom of the base-plate. An instrument control panel with electrical circuits is attached to the rod. One end of a supporting arm (3) is attached to the top of the rod. The other end of the supporting arm (3) is connected to the radiation generator and its accessories. Optionally, earphone (5) for a music playback system and accupoints stimulating electrodes (6) may also be electrically connected to the instruments control panel.

The radiation generator (8) comprises a heat resistant, insulating substrate (13) disposed in the center of a reflective protective cover (9), coated with a transducing layer (12) and deposited thereon, a radiation generating layer (11) the transducing layer (12) being electrically connected to a transducing control circuit which is in turn connected to a power source. The radiation generator (8) is supported by struts in the supporting arm (3).

The radiation generating layer (11) was prepared as follows: the above named fourteen constituents are prepared in selected proportions, mixed and pulverized in a ball mill into powder of 50 mesh. The pulverized mixture was calcined for 3 hours at a temperature of 1140° C., removed and again pulverized in a ball mill into a powder of 50 mesh. An effective amount of a binder, such as silicasol, was added to the powder and stirred homogenously to form a paste which was coated onto the surface of the transducing layer (12). The substrate with the transducing layer and radiation generating layer was then placed into a preheated oven at about 150° C. and allowed to solidify for 1 hour.

The transducing layer (12) was prepared as follows: tin tetrachloride, antimony trichloride and iron trichloride were mixed in a ratio of tin tetrachloride:antimony trichloride:iron trichloride=105:0.8:1 in a small amount of water to form an aqueous solution, which was evenly coated on the cleaned substrate (13) of the radiation generator. The coated substrate was heated at a temperature of 800° C. The metal chloride mixture was hydrolyzed and oxidized to generate an electrical semiconductive layer of metallic oxides, on the surface of the substrate (13). Thereafter, electrical connecting means in the form of two electrodes embedded in the substrate were silver plated to reduce the contact resistance between the transducing layer (12) and the power supply.

When charged with electricity, the transducing layer acts as a semi-conductor to transfer energy to the radiation generating layer (11). The amount of power transmitted by the transducing layer is determined by its surface resistance. In the above described embodiment it is 3000 ohms.

The substrate (13) of the radiation generator is prepared from any known common heat-resistant, insulating material. It is formed and embedded therein with electrical connecting means to connect the transducing layer to a transduction control circuit designed as required.

The reflective protective cover (9) may be formed from an aluminum sheet with thickness of 0.8–1 mm. by extrusion molding into a conical or half tubular shape. It is provided with a protective window plate or network over the open part of the reflective cover. In the present embodiment, the reflective cover is 300 mm. long, 120 mm. wide and 50 mm. thick. The internal surface can be anodized and polished. The radiation generator is also attached to the reflective protective cover by means of fixed struts (10) and connected through wiring to a power supply. The wiring must be able to withstand high temperatures.

The music source may be a stereophonic system with earphones (5). The accupoints stimulating electrodes may be controlled by the music to provide stimulating currents into the accupoints of the body. Different types of music may be provided to different patients.

The following examples illustrate the present invention for treating various disease conditions.

(1) Chilblains and Frostbite

If there are broken or infected surfaces, the wound must be first cleaned and dried as much as possible. The infected part is exposed to the radiation generating apparatus for about 15 to 60 minutes. The distance between the generator and the affected part is about 50 to 500mm. The effective area of the generator should be sufficiently large to cover the affected area. The optimum treating dosage is selected based on the acceptable intensity of the field for the patient, with the treating voltage generally set between about 80 to 200 volts. Ordinarily, the treatment is repeated an average of about 2 to 7 times. Relieve from itching and pain, and drying of the affected part are generally achieve on the first day.

(2) Chronic Skin Ulcers Caused by Vasculitis and Varix of the Lower Limbs.

If there is secretion from the ulcerated part, the surface of part must be first cleaned and dried before treatment. The generator should be in a concave arc adapted to the form of the affected limbs. The effective area of the generator should cover the affected limbs at a distance of between about 50 to 500 mm. The optimum treating voltage is set at a level to provide a comfortable warm feeling for the patient. It is generally at about 80–150 volts. Ordinarily, improvement are obtained after 3 to 10 treatments. Complete cures may be effective over a longer period of time.

(3) Bronchitis and Asthma.

The apparatus of this invention is used to irradiate the upper chest, the back, and the esophagus. The optimum treating dosage is selected to provide a comfortable feeling for the patient. The average voltage is about 100–180 volts. The distance between the generator and the affected parts is about 150–300 mm. Curative effects are generally achieved after 3–5 treatments. For some patients, the symptoms will disappear at this time. However, for most patients full recovery requires treatment for about 15 to 30 days.

(4) Diseases in the Areas of Gynaecology and Obstetrics.

For dysmenorrhoea, the apparatus of this invention is used to irradiate the abdomen or related accupoints. The optimum treating voltage is selected to provide a comfortable feeling for the patient. For most patients relief is obtained after only 1–2 treatments.

For pelvitis, surgical wounds from caesarean section, laceration in the vulva or birth canal, the apparatus can be used to irradiate directly the affected parts. The distance between the generator and the affected parts is about 50 to 500 mm. and the treating voltage is generally about 100–200 volts. For lacerations and wounds treated with the apparatus by the method of the present invention healing periods are generally shortened by about 20% as compared with normal healing periods.

A partial clinical record of treated cases by using an experimental apparatus of this invention is shown on Table 1.

In another embodiment of this invention, dual purpose lamp designed to provide a radiation generator and a lamp are illustrated as follows:

EXAMPLE 1

A Unitary Holder for a Single-Group Treatment Radiation Generator and Lighting Lamp This treatment lamp consist of a pedestal (21) to which is fixably attached a flexible rod (22) connected to a support (23) for a single-group treatment generator (24) or a light bulb. The bottom of the rod which is of a plastic hose type, and fixably attached to the pedestal (21) to which an electric control system is mounted. A unilateral and single-group treatment generator receptacle containing therein electrical connections to the electric control system, is attached to the top of the rod.

The single-group treatment generator comprises a tubular substrate (26) provided with electrical connecting means and coated with a transducing layer (27), on which is deposited a radiation generating layer. The radiation generating layer is prepared as described above in proportions selected for Group I mixture. The generator is mounted under a protective network (29) in the center of a reflective cover (30) to a receptacle for an ordinary light bulb. The receptable contains electrical connecting means such that the transducing layer (21) is electrically connected to the transduction control panel.

The support for the single-group treatment bulb is provided with a unitary protective cover (32) and the receptacle (31) for a general purpose light bulb is mounted in the support. When this lamp is used for general illumination, a general purpose light bulb with threaded connection is screwed into the receptable (31). When it is used for radiation treatment, a single-group treatment radiation generator having a threaded connection can be screwed into the receptable (31).

Since the radiation generator (28) is prepared with a Group I mixture described above, relief for the generator provides diseases of the blood circulatory system. For treatment of surgical wounds, skin diseases as well as arthritis, a generator with a Group II mixture should be used (28). For treatment of autonomic neurotic diseases a generator prepared with a Group III mixture should be used.

EXAMPLE 2

A Binary Holder for a Single-Group Treatment and Lighting Lamp

Figure 5:
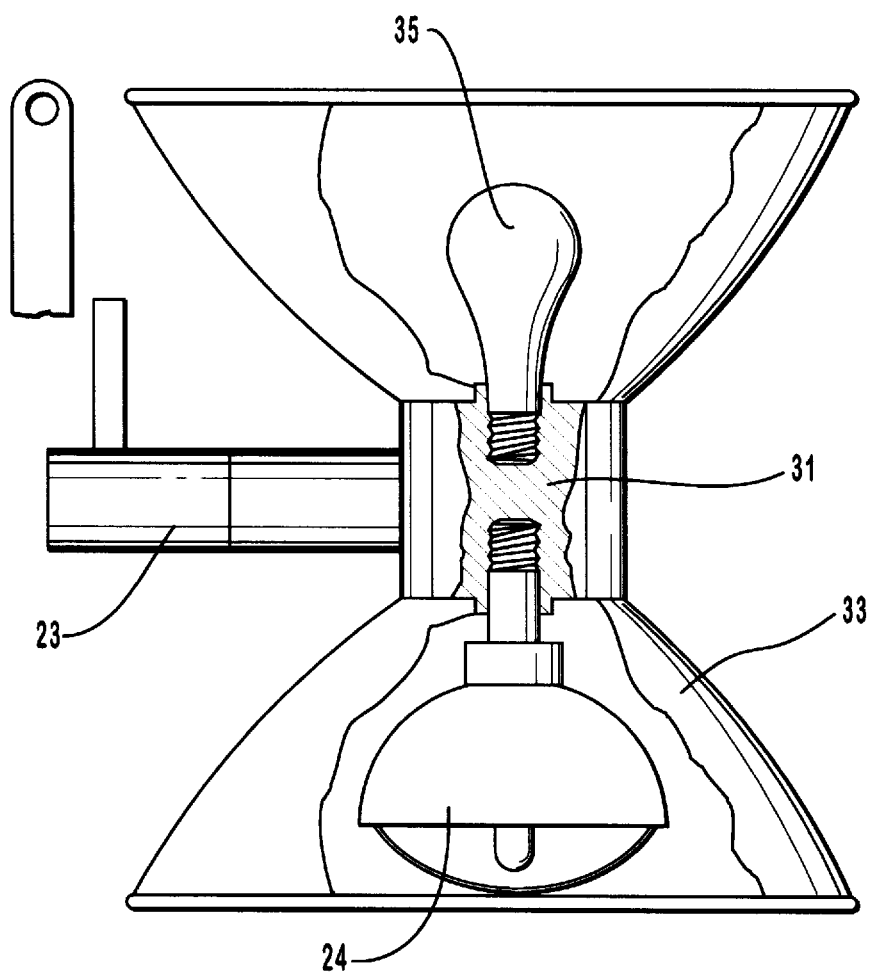
FIG. 5 is a perspective view of a binary holder for a light bulb and a single-group treatment generator of a dual purpose treatment and lighting lamp.
Figure 6:
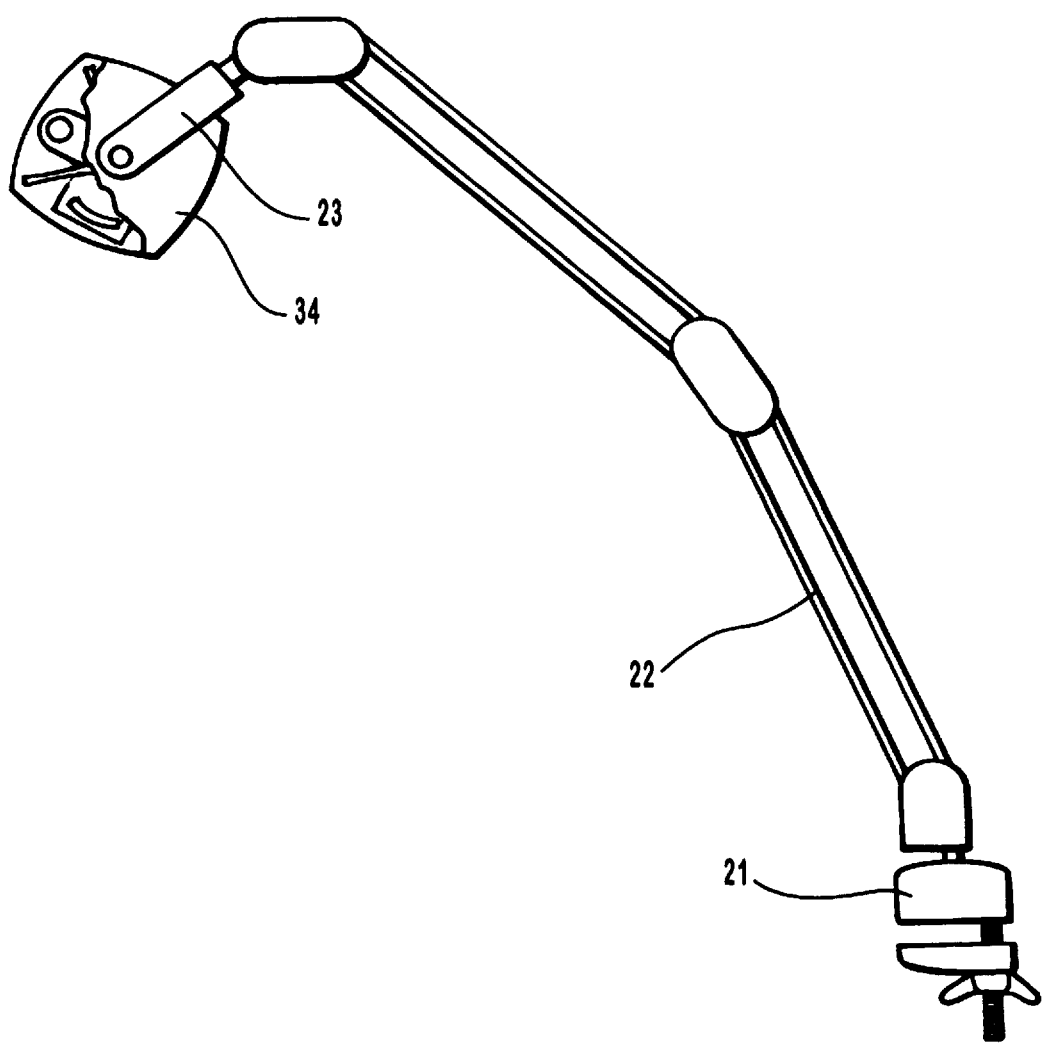
FIG. 6 is a perspective view of a multi-group treatment and lighting lamp with a holder for a plurality of treatment generators and a light bulb.

The parts for the binary holder single-group treatment and lighting lamp are essentially the same as the lamp described in Example 1 except for the followings:

Binary lamp covers (33) and receptacles for a general purpose light bulb arid a radiation generator are placed back to back. See FIG. 5.

EXAMPLE 3

A Ternary Holder For Two Group Treatments and Lighting Lamp

For a ternary holder for a two radiation treatments and lighting lamp, the lamp of Example 1 is modified. The bottom of the rod (22) is connected to a clamp pedestal (21). The top of the rod (22) is connected to a rotatable ternary holder. The electric control system is mounted in the clamp pedestal (21) and connected electrically with the receptacles in the rotatable support.

Figure 7A:
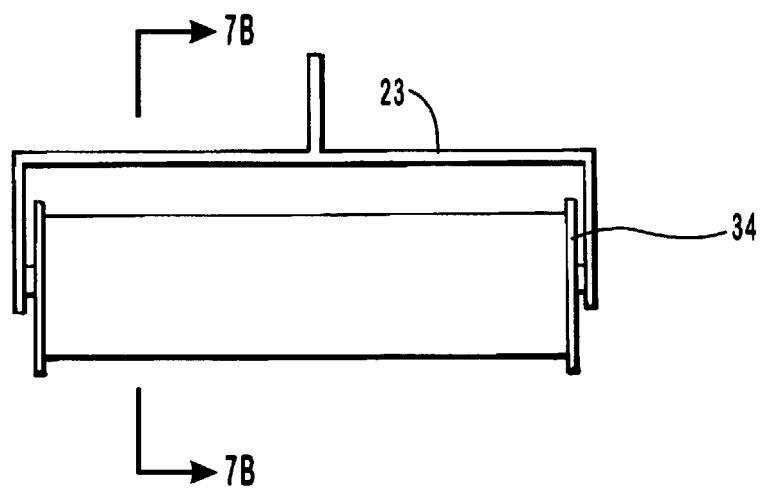
Figure 7B:
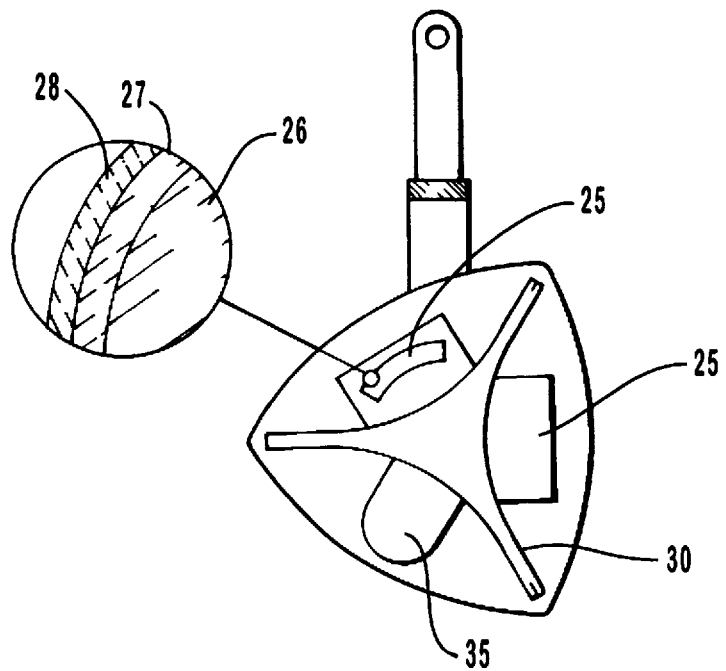

The rotatable support (23) comprises a rotatable hinge (34) which holds in position each of the three compartments of the reflective cover (30). Each of the tubular compartments of the reflective cover (30) is concave in cross section, and connected back to back at the outer edges as shown in FIG. 7. Two tubular generators (25) are placed in each of the two receptable in the three compartments of the cover and a reflective tubular bulb lamp (35) is placed in the third. The radiation generating layer (2) of the two generators (25) may be made from any two of the three Groups I, II or III mixtures.

EXAMPLE 4

A Quaternary Holder For Three Group Treatments and Lighting Lamp

Figure 8A:
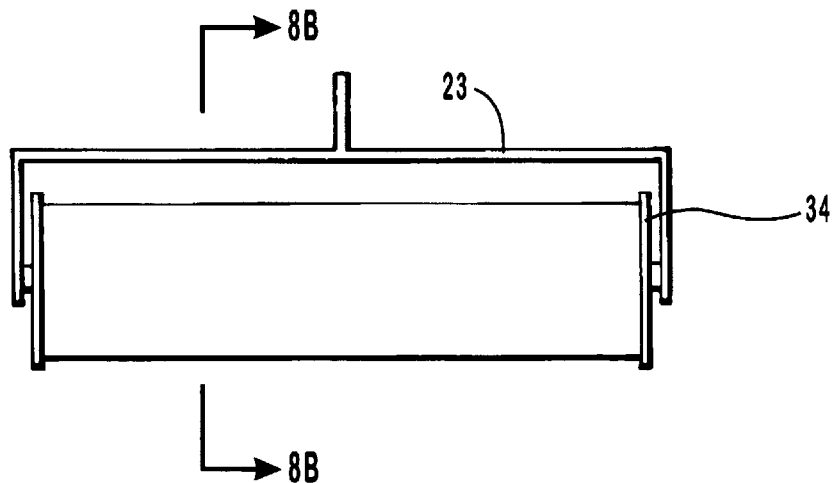
FIGS. 8a and 8b are partial views of a quaternary holder for three radiation generators and a light bulb.
Figure 8B:
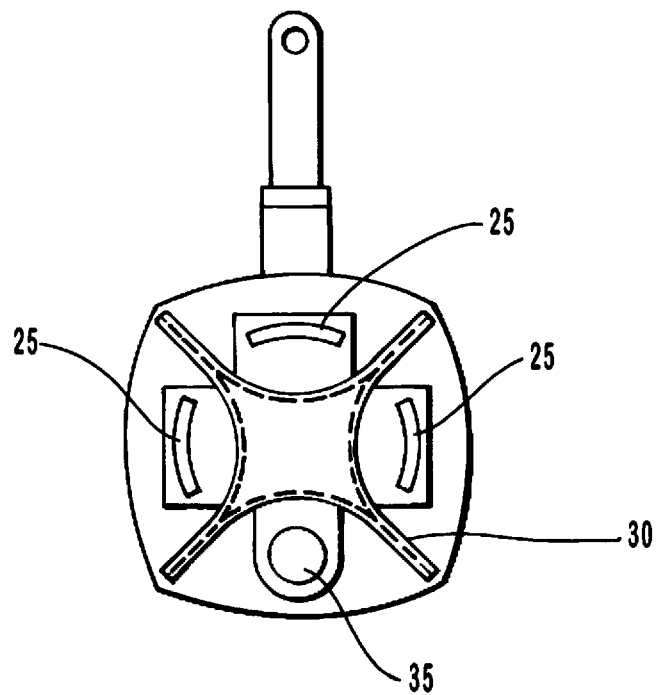
Figure 9:
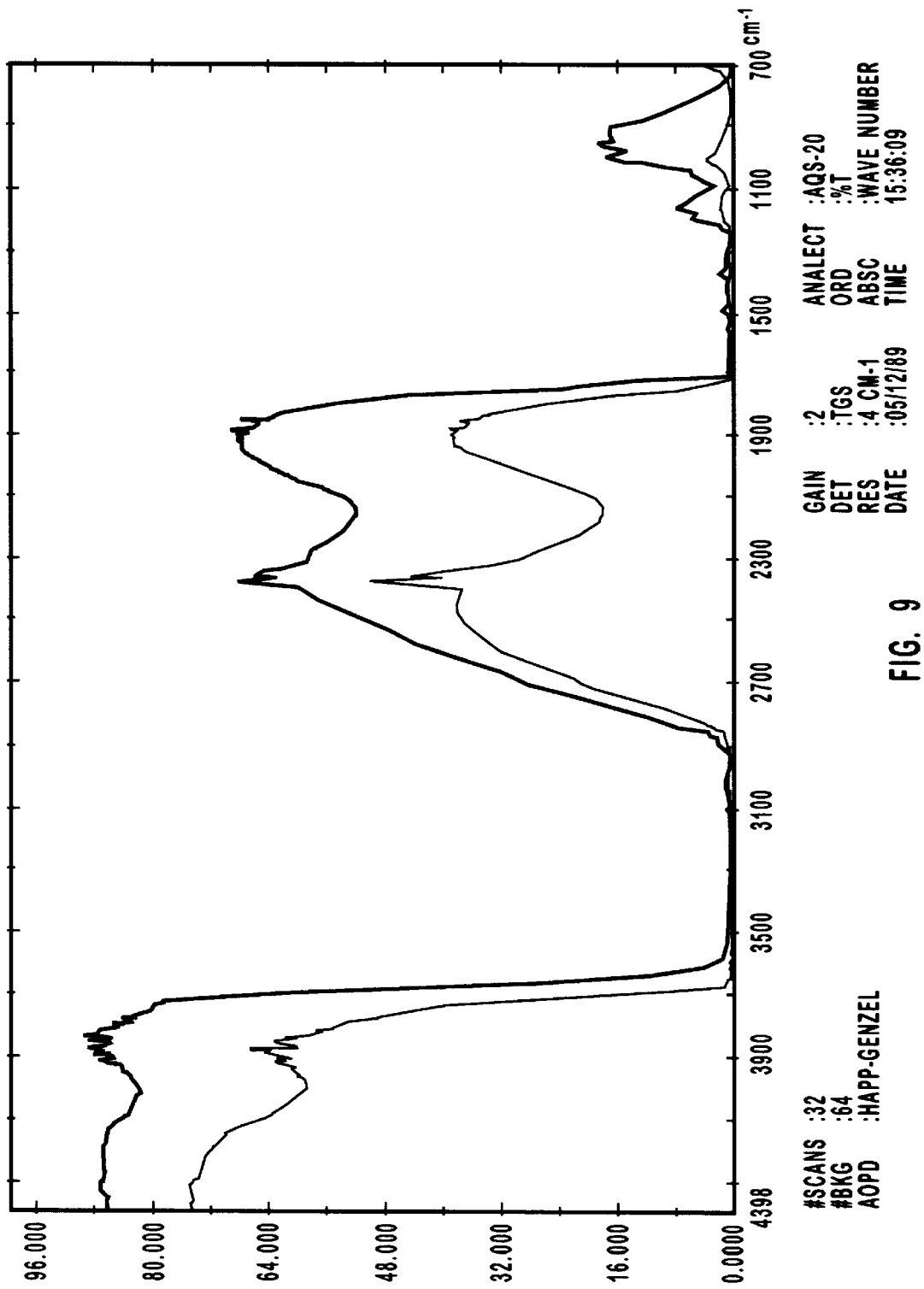
Figure 10:
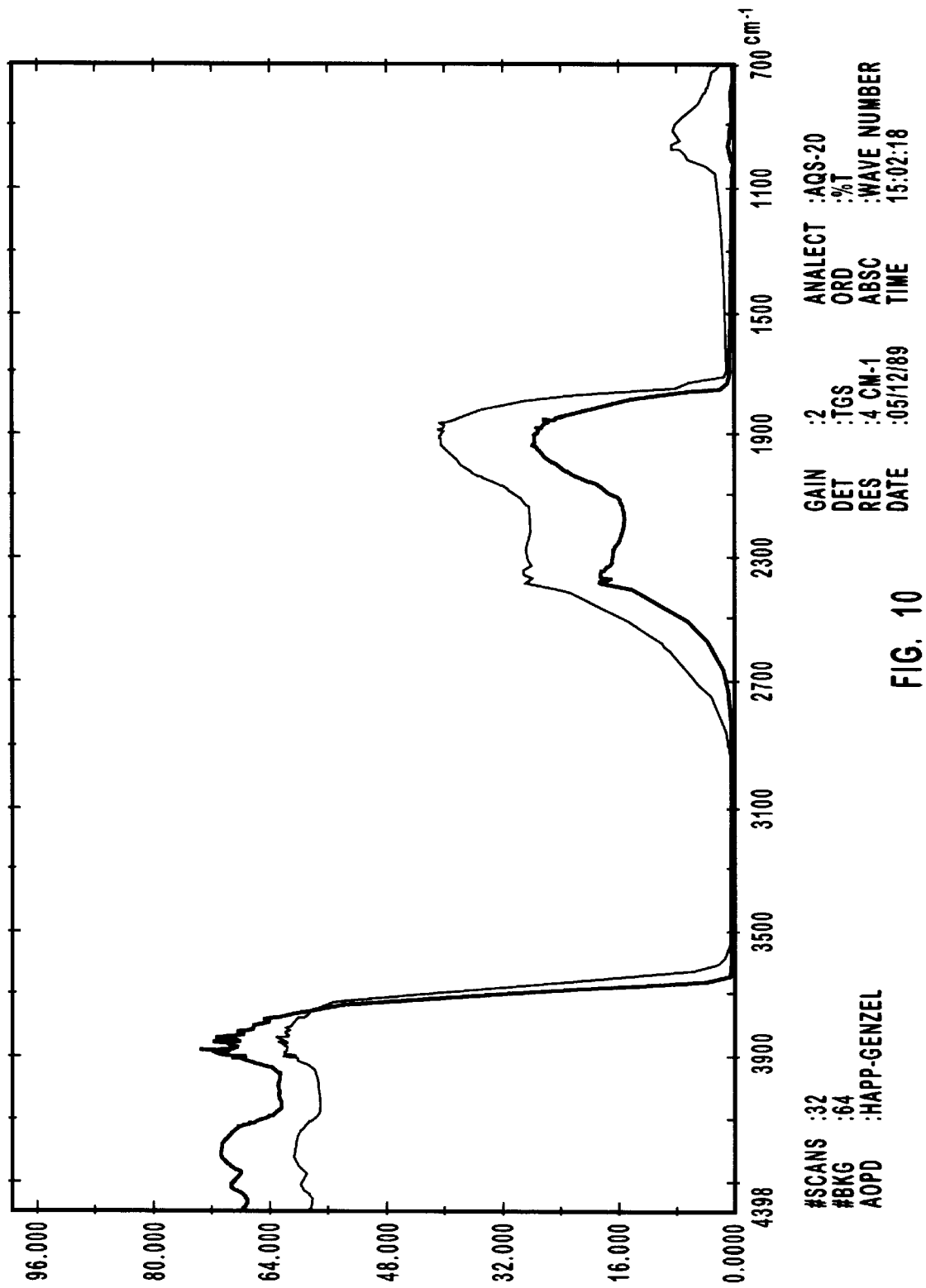
Figure 11:
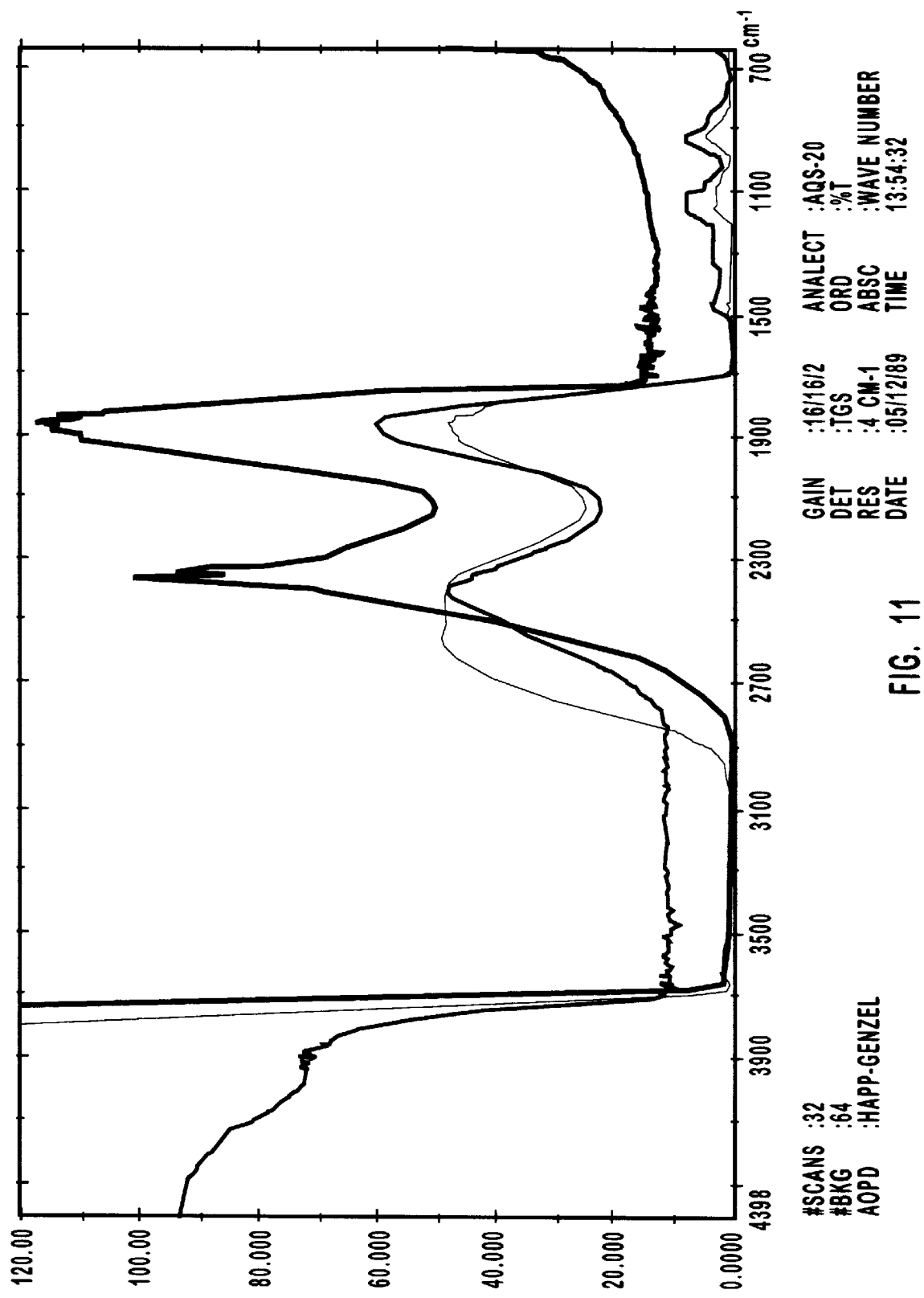
Figure 12:
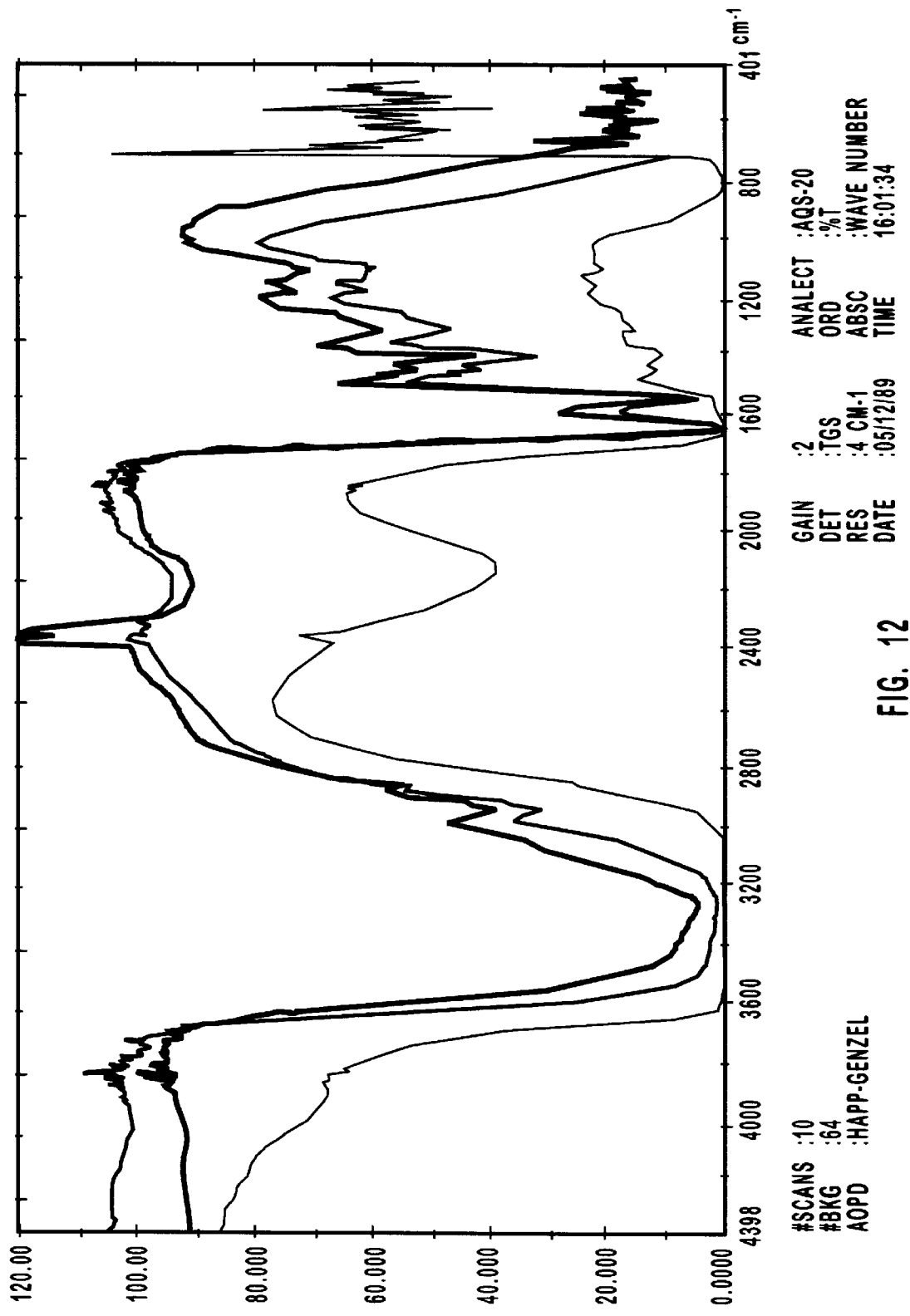

The quaternary holder lamp is similar to the ternary holder lamp described in Example 3 except for the following:

The rotatable support (23) comprises a rotatable support hinge (34) holding a reflective cover (30) with four compartments. Each of the four tubular compartments in the reflex cover (30) is concave and connected back to back on the outer edges as shown in FIG. 8. Each of the three tubular generators has a radiation generating layer (28) made from one of Group I, II, or III mixtures. The generators in tubular form are placed in receptacles in the three of the compartments of the reflective cover while a tubular light bulb is placed in the fourth.

The radiation generator of the present invention is also suitable for treatment of stubborn chronic diseases. Moreover, other suitable embodiments may be made. For instance, the surface may be prepared from enamel or sprayed with a protective film. The excitation energy may also be provided by other energy sources, such as heating fuel or radiation.

The above examples illustrates the invention and are riot to be construed as limiting the scope thereof.

What is claimed is:

1. A method of generating an electromagnetic radiation and a thermal convention radiation to have a therapeutic effect on a living organism, comprising the steps of:
   (a) providing a means for supplying electrical power;
   (b) providing a transducing circuit control means connected to the power supply means;
   (c) forming a substrate from a heat resistant insulating material and providing therein means for electrical connection;
   (d) connecting an end of the electrical connection means to the transducing circuit control means;
   (e) coating a transducing layer on the substrate such that the transducing layer is in contact with the other end of the electrical connection means in the substrate, the transducing layer comprising a mixture of about 80–120 parts by weight of tin tetrachloride, about 0.5 to 2 parts by weight of antimony trichloride and about 0.3 to 2.5 parts by weight of iron trichloride;
   (f) heating the substrate and the transducing layer at a temperature of about 600° to 900° C. for about 1–6 hours, and then cooling to room temperature;
   (g) evenly coating the transducing layer with a radiation generating layer comprising a homogeneous mixture of magnesium oxide, iron oxide, manganese oxide, molybdenum oxide, zinc oxide, lithium oxide, copper oxide, titanium oxide, strontium oxide, chromium oxide, cobalt oxide, vanadium oxide, chromium metal and mixed rare-earth elements and/or compounds in a proportion by weight of about 0.5–8%: about 7–30%: about 0–6%; about 0.6–5%; about 1–17%; about 0–4%: about 1–7%: about 0–7%: about 0–5.5%: about 25–85%: about 0–5%: about 0–10%: about 0.5–4%: about 0–40%,
   (h) generating the electromagnetic radiation and the thermal convention radiation from the radiation generating layer by electrically resistance heating the transducing layer on the substrate with the power supply means through the electrical connection means; and
   (i) directing both the electromagnetic radiation and the thermal convention radiation generated by the radiation generating layer to contact the living organism; whereby the electromagnetic radiation and the thermal convention radiation has a therapeutic effect on the living organism.

2. The method according to claim 1, wherein the transducing layer is made from a mixture of about 105 parts by weight of tin tetrachoride, 0.8 part by weight of antimony trichloride and 1 part by weight of iron trichloride.

3. The method according to claim 2, wherein the radiation generating layer comprises a homogeneous mixture of magnesium oxide, iron oxide, manganese oxide, molybdenum oxide, zinc oxide, lithium oxide, copper oxide, titanium oxide, strontium oxide, chromium oxide, cobalt oxide, vanadium oxide, chromium metal and mixed rare-earth elements and/or compounds in a ratio by weight of 1:20:2:3:4:0.5:1:1.5:0.5:45:0.5:10:1:10.

4. The method according to claim 2, wherein the radiation layer comprises a homogeneous mixture of magnesium oxide, iron oxide, molybdenum oxide, zinc oxide, lithium oxide, copper oxide, titanium oxide, strontium oxide, cobalt oxide, vanadium oxide, chromium metal and mixed rare-earth elements and/or compounds in a ratio by weight of 2:30:0.6:1.5:1.2:2:1.2:37:0.3:5:1.2:12.

5. The method according to claim 2, wherein the radiation generating layer comprises a homogeneous mixture of magnesium oxide, iron oxide, manganese oxide, molybdenum oxide, zinc oxide, lithium oxide, copper oxide, titanium oxide, strontium oxide, chromium oxide, chromium metal and mixed rare-earth elements and/or compounds in a ratio by weight of 0.5:25:3:2:7:2:1.5:1:1:55:1.5:0.5.

6. A method of according to claim 2, where the radiation generating layer comprises a homogeneous mixture of magnesium oxide, iron oxide, manganese oxide, molybdenum oxide, zinc oxide, copper oxide, chromium oxide, cobalt oxide, vanadium oxide, chromium metal and mixed rare-earth elements and/or compounds in a ratio by weight of 1.5:15:1:1.5:5:1.6:62:0.7:3:0.7:8.

7. The method according to claim 2, wherein the transducing layer is prepared by homogeneously mixing pulverized tin tetrachloride, antimony trichloride and iron trichloride in a proportion by weight of 105:0.8:1, solubilizing in an effective amount of water and evenly sprayed on the substate, the coated substate is then heated at 800° C. for 3 hours.

8. The method according to claim 1, wherein the radiation generating layer comprises a homogeneous mixture of magnesium oxide, iron oxide, manganese oxide, molybdenum oxide, zinc oxide, lithium oxide, copper oxide, titanium oxide, strontium oxide, chromium oxide, cobalt oxide, vanadium oxide, chromium metal and mixed rare-earth elements and/or compounds in a ratio by weight of 1:20:2:3:4:0.5:1:1.5:0.5:45:0.5:10:1:10.

9. The method according to claim 1, wherein the radiation layer comprises a homogeneous mixture of magnesium oxide, iron oxide, molybdenum oxide, zinc oxide, lithium oxide, copper oxide, titanium oxide, strontium oxide, cobalt oxide, vanadium oxide, chromium metal and mixed rare-earth elements and/or compounds in a ratio by weight of 2:30:0.6:1.5:1.2:2:1.2:37:0.3:5:1.2:12.

10. The method according to claim 1, wherein the radiation generating layer comprises a homogeneous mixture of magnesium oxide, iron oxide, manganese oxide, molybdenum oxide, zinc oxide, lithium oxide, copper oxide, titanium oxide, strontium oxide, chromium oxide, chromium metal and mixed rare-earth elements and/or compounds in a ratio by weight of 0.5:25:3:2:7:2:1.5:1:1:55:1.5:0.5.

11. The method according to claim 1, wherein the radiation generating layer comprises a homogeneous mixture of magnesium oxide, iron oxide, manganese oxide, molybdenum oxide, zinc oxide, copper oxide, chromium oxide, cobalt oxide, vanadium oxide, chromium metal and mixed rare-earth elements and/or compounds in a ratio by weight of 1.5:15:1:1.5:5:1.6:62:0.7:3:0.7:8.

12. The method according to claim 1, wherein the transducing layer is prepared by homogeneously mixing pulverized tin tetrachloride, antimony trichloride and iron trichloride in a proportion by weight of 105:0.8:1, solubilizing in an effective amount of water and evenly sprayed on the substate, the coated substate is then heated at 800° C. for 3 hours.

13. The method according to claim 1, wherein the radiation generating layer is made from a homogenous mixture having a composition selected from a group consisting of magnesium oxide, iron oxide, molybdenum oxide, zinc oxide, lithium oxide, copper oxide, titanium oxide, strontium oxide, chromium oxide, cobalt oxide, vanadium oxide, chromium metal, mixed rare earth elements and/or compounds in a ratio by weight of 2:30:0.6:6:1.5:1.2:2:1.2:37:0.3:5:1.2:12.

14. The method according to claim 1, wherein the radiation generating layer is made from a homogenous mixture having a composition selected from a group consisting of magnesium oxide, iron oxide, manganese oxide, molybdenum oxide, zinc oxide, lithium oxide, copper oxide, titanium oxide, strontium oxide, chromium oxide, chromium metal and mixed-earth elements and/or compounds in a ratio by weight of 0.5:25:3:2:7:2:1.5:1:1:55:1.5:0.5.

15. The method according to claim 1, wherein the radiation generating layer is made from a homogenous mixture having a composition selected from a group consisting of magnesium oxide, iron oxide, manganese oxide, molybdenum oxide, zinc oxide, copper oxide, chromium oxide, cobalt oxide, vanadium oxide, chromium metal, rare-earth elements and/or compounds in a ratio by weight of 1.5:15:1:1.5:5:1.6:62:0.7:3:0.7:8.

16. The method according to claim 1, wherein the radiation generating layer is made from a homogenous mixture having a composition selected from a group consisting of magnesium oxide, iron oxide, manganese oxide, molybdenum oxide, zinc oxide, lithium oxide, copper oxide, titanium oxide, strontium oxide, chromium oxide, cobalt oxide, vanadium oxide, chromium metal, mixed rare-earth elements and/or compounds in a ratio by weight of 1:20:2:3:4:0.5:1:1:0.5:45:0.5:10:1:10.

17. The method according to claim 1, wherein a surface area on the living organism is contacted by the directing both the electromagnetic radiation and the thermal convention radiation generated by the radiation generating layer, and wherein the radiation generating layer has a surface area that is less than or equal to the surface area on the living organism that is contacted by the directing both the electromagnetic radiation and the thermal convection radiation generated by the radiation generating layer, the transducing layer having a surface area that is greater than or equal to the surface area of the radiation generating layer, and the substrate having a surface area that is greater than or equal to the surface area of the transducing layer.

18. A method for generating an electromagnetic radiation and a thermal convention radiation useful to have a therapeutic effect on a living organism, comprising the steps of:

(a) providing a means for supplying electrical power;

(b) providing a transducing circuit control means connected to the power supply means;

(c) forming a substrate from a heat resistant insulating material and providing therein means for electrical connection;

(d) connecting an end of the electrical connection means to the transducing circuit control means;

(e) coating a transducing layer on the substrate such that the transducing layer is in contact with the other end of the electrical connection means in the substrate, the transducing layer comprising a mixture of about 80–120 parts by weight of tin tetrachloride, about 0.5 to 2 parts by weight of antimony trichloride and about 0.3 to 2.5 parts by weight of iron trichloride;

(f) heating the substrate and the transducing layer at a temperature of about 600° to 900° C. for about 1–6 hours, and then cooling to room temperature;

(g) evenly coating the transducing layer with a radiation generating layer comprising a homogeneous mixture of magnesium oxide, iron oxide, manganese oxide, molybdenum oxide, zinc oxide, lithium oxide, copper oxide, titanium oxide, strontium oxide, chromium oxide, cobalt oxide, vanadium oxide, chromium metal and mixed rare-earth elements and/or compounds in a proportion by weight of about 0.5–8%: about 7–30%: about 0–6%; about 0.6–5%; about 1–17%; about 0–4%: about 1–7%: about 0–7%: about 0–5.5%: about 25–85%: about 0–5%: about 0–10%: about 0.5–4%: about 0–40%, said radiation generating layer being made from a homogenous mixture having a composition selected from a group consisting of magnesium oxide, iron oxide, molybdenum oxide, zinc oxide, lithium oxide, copper oxide, titanium oxide, strontium oxide, chromium oxide, cobalt oxide, vanadium oxide, chromium metal, mixed rare earth elements and/or compounds in a ratio by weight of 2:30:0.6:6:1.5:1.2:2:1.2:37:0.3:5:1.2:12; and (h) generating the electromagnetic radiation and the thermal convention radiation from the radiation generating layer by electrically resistance heating the transducing layer on the substrate with the power supply means through the electrical connection means.

19. The method according to claim 18, further comprising:

directing both the electromagnetic radiation and the thermal convention radiation generated by the radiation generating layer to contact the living organism; whereby the electromagnetic radiation and the thermal convention radiation has a therapeutic effect on the living organism.

20. A method of generating an electromagnetic radiation and a thermal convention radiation to have a therapeutic effect on a living organism, comprising the steps of:

(a) providing a substrate having thereon a radiation generating layer comprising a homogeneous mixture of magnesium oxide, iron oxide, manganese oxide, molybdenum oxide, zinc oxide, lithium oxide, copper oxide, titanium oxide, strontium oxide, chromium oxide, cobalt oxide, vanadium oxide, chromium metal and mixed rare-earth elements and/or compounds in a proportion by weight of about 0.5–8%: about 7–30%: about 0–6%; about 0.6–5%; about 1–17%; about 0–4%: about 1–7%: about 0–7%: about 0–5.5%: about 25–85%: about 0–5%: about 0–10%: about 0.5–4%: about 0–40%;

(b) applying power to the radiation generating layer with a means for supplying power so as to generate the electromagnetic radiation and the thermal convention radiation from the radiation generating layer; and (c) directing both the electromagnetic radiation and the thermal convention radiation generated by the radiation generating layer to contact the living organism; whereby the electromagnetic radiation and the thermal convention radiation has a therapeutic effect on the living organism.

* * * * *

UNITED STATES PATENT AND TRADEMARK OFFICE
CERTIFICATE OF CORRECTION

Page 1 of 2

PATENT NO. : 5,849,026
DATED : Dec. 15, 1998
INVENTOR(S) : Lin Zhou; Xue-shan Zhang It is certified that error appears in the above-identified patent and that said Letters Patent is hereby corrected as shown below:

Col. 1, line 4, delete the second occurrence of "which"

Col. 1, line 43, after "physiotherapy" change "methods" to --method--

Col. 1, line 62, after "devices" change "utilizes" to --utilize--

Col. 2, line 34, after "invention" insert --is--

Col. 2, line 36, after "into" change "accounts" to --account--

Col. 3, line 16, after "with" insert --the--

Col. 5, line 27, after "with" insert --the--

Col. 5, line 63, after "transducing" change "layer a" to --layer. A--

Col. 6, line 53, after "and" change "maybe" to --may be--

Col. 6, line 57, after "mixed" change "is" to --in--

Col. 9, line 7, after "Further" insert a comma

Col. 10, line 49, after "attached" change "Lo" to --to--

Col. 11, line 62, after "times." change "Relieve" to --Relief--

Col. 11, line 63, after "generally" change "achieve" to --achieved--

UNITED STATES PATENT AND TRADEMARK OFFICE
CERTIFICATE OF CORRECTION

PATENT NO. : 5,849,026
DATED : Dec. 15, 1998
INVENTOR(S) : Lin Zhou; Xue-shan Zhang It is certified that error appears in the above-identified patent and that said Letters Patent is hereby corrected as shown below:

Col. 12, line 7, before "obtained" change "are" to --is--

Col. 13, line 24, after "bulb" change "arid" to --and--

Col. 13, line 31, after "for" delete "a"

Col. 14, line 58, after "of tin" change "tetrachoride" to --tetrachloride--

Col. 15, line 27, change both occurrences of "substate" to --substrate--

Col. 15, line 63, change both occurrences of "substate" to --substrate--

Col. 16, line 32, after "by" delete "the"

Col. 16, line 37, after "by" delete "the"

Signed and Sealed this

Eighteenth Day of April, 2000

Attest:

Q. TODD DICKINSON

*Attesting Officer*   *Director of Patents and Trademarks*